United States Patent
Aistrup et al.

(10) Patent No.: US 9,456,969 B2
(45) Date of Patent: Oct. 4, 2016

(54) SCALP CARE COMPOSITION

(71) Applicant: The Procter & Gamble Company, Cincinnati, OH (US)

(72) Inventors: Elizabeth Rebecca Aistrup, Cincinnati, OH (US); James Robert Schwartz, West Chester, PA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/478,305

(22) Filed: Sep. 5, 2014

(65) Prior Publication Data

US 2015/0065476 A1 Mar. 5, 2015

Related U.S. Application Data

(60) Provisional application No. 61/874,094, filed on Sep. 5, 2013.

(51) Int. Cl.
*A61K 8/27* (2006.01)
*A61K 8/34* (2006.01)
*A61Q 5/00* (2006.01)
*A61K 8/81* (2006.01)
*A61K 8/49* (2006.01)

(52) U.S. Cl.
CPC .......... *A61K 8/345* (2013.01); *A61K 8/27* (2013.01); *A61K 8/4933* (2013.01); *A61K 8/8141* (2013.01); *A61K 8/8147* (2013.01); *A61K 8/8152* (2013.01); *A61K 8/8158* (2013.01); *A61Q 5/006* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 4,329,334 A | 5/1982 | Su et al. | |
| 4,867,971 A | 9/1989 | Ryan et al. | |
| 6,284,234 B1 | 9/2001 | Niemiec et al. | |
| 6,908,912 B2 | 6/2005 | Rioux et al. | |
| 7,001,594 B1 | 2/2006 | Peffly et al. | |
| 7,026,308 B1 | 4/2006 | Gavin et al. | |
| 7,455,851 B1 | 11/2008 | Nelson et al. | |
| 7,674,785 B2 | 3/2010 | Gavin et al. | |
| 8,206,732 B2 | 6/2012 | Nelson et al. | |
| 8,313,782 B2 | 11/2012 | Guthery | |
| D681,876 S | 5/2013 | Murdock et al. | |
| D690,876 S | 10/2013 | Murdock et al. | |
| 8,679,552 B2 | 3/2014 | Guthery | |
| 8,796,252 B2 | 8/2014 | Rioux et al. | |
| 8,858,968 B2 | 10/2014 | Potin | |
| 2003/0008855 A1 | 1/2003 | Simon et al. | |
| 2003/0157088 A1 | 8/2003 | Elliott et al. | |
| 2003/0180242 A1 | 9/2003 | Eccard et al. | |
| 2009/0264449 A1 | 10/2009 | Iwata et al. | |
| 2011/0268684 A1* | 11/2011 | Battermann et al. | 424/70.11 |
| 2012/0103151 A1 | 5/2012 | Jones et al. | |
| 2012/0134948 A1 | 5/2012 | Springer et al. | |
| 2012/0251627 A1 | 10/2012 | Nelson et al. | |
| 2013/0115315 A1 | 5/2013 | Derkx | |
| 2013/0284195 A1 | 10/2013 | Murdock et al. | |
| 2014/0349902 A1* | 11/2014 | Allef et al. | 510/119 |
| 2015/0065476 A1 | 3/2015 | Aistrup et al. | |
| 2015/0306006 A1 | 10/2015 | Aistrup et al. | |

FOREIGN PATENT DOCUMENTS

| | | |
|---|---|---|
| EP | 0639368 A1 | 2/1995 |
| EP | 0914816 A1 | 5/1999 |
| FR | 2976801 B1 | 7/2013 |
| JP | 2005-206538 | 8/2005 |
| WO | WO 2007/010478 A2 | 1/2007 |
| WO | WO 2010/018418 A1 | 2/2010 |
| WO | WO 2013/050241 A1 | 4/2013 |

OTHER PUBLICATIONS

PCT International Search Report and Written Opinion for PCT/US2015/027410, dated Jul. 15, 2015.
PCT International Search Report and Written Opinion for PCT/US2014/054270, dated Nov. 20, 2014.
"Soothing Serum", Mintel GNPD, Nioxin Research Laboratories, Feb. 2009.
"2-in-1 anti-dandruff & styling gel", Mintel GNPD, Schwarzkopf & DEP, Nov. 2004.
"Gel", Mintel GNPD, Davines, Apr. 2012.

* cited by examiner

*Primary Examiner* — Robert A Wax
*Assistant Examiner* — Quanglong Truong
(74) *Attorney, Agent, or Firm* — Linda M. Sivik

(57) ABSTRACT

A scalp care composition comprising from 1% to 99% of a volatile carrier; from 0.05% to 10% of a polymeric rheology modifier and mixtures thereof; from 0.03% to 1% of particulate scalp benefit agent wherein the composition is shear thinning and has (1) a zero shear viscosity value measured at 0.01 Pa of greater than about 1,500 Pa s; (2) a moderate stress viscosity value measured at 1 Pa viscosity of greater than about 1,000 Pa s; and (3) a high shear rate viscosity value measured at 100 l/s of less than about 0.5 Pa s.

12 Claims, No Drawings

SCALP CARE COMPOSITION

FIELD OF THE INVENTION

The present invention relates to a scalp care compositions comprising one or more actives useful for treating dandruff.

BACKGROUND OF THE INVENTION

Hair and scalp leave on treatment compositions comprising various combinations of hair and scalp actives, are known in the art and are commercially available. These compositions may have rheological parameters that optimize the consumer perceived usage experience (spread, coverage, etc.).

Anti-dandruff hair rinse off products are also commercially available. Anti-dandruff shampoos, conditioners, and other rinse off treatments typically incorporate an anti-dandruff active. One type of anti-dandruff agents are particulate, crystalline anti-dandruff agents, such as sulfur, selenium disulfide and heavy metal salts of pyridinethione. Soluble anti-dandruff agents, such as ketoconazole, are also available.

Nevertheless, some consumers desire an anti-dandruff leave on treatment which provides a level of anti-dandruff efficacy that can replace other anti-dandruff rinse off products or be in addition to rinse off anti-dandruff products or provide leave on benefits to hair and scalp that are difficult to achieve with a rinse off product. Consequently, a need exists for a treatment product that combines core anti-dandruff efficacy with additional scalp health and hair benefits that the consumer can notice and feel, i.e. effective, and is delightful to use.

Such an invention should be able to reasonably easily cover the majority of the affected area, such as the scalp, with each application in order to provide the necessary benefit. Such an invention should also be able to remain near the site of application for a reasonable amount of time after application, such that it can deliver the necessary anti-dandruff or scalp benefit actives without dripping, running, or transferring to another location. Finally, such an invention should remain homogeneous across a typical packaging from top to bottom in reasonable environmental conditions so that each application contains and delivers the necessary amount of actives to the affected areas.

For example, one means to achieve excellent coverage of the affected area, such as the scalp, is to deliver actives via a carrier that does not utilize a rheological modifier, or does so in such a way that rheological parameters such as viscosity are low. However, such compositions would not stay where applied and would drip, run, or transfer to other areas in a manner such as to reduce its effectiveness. Thus, it has heretofore been believed that an adequate level of rheological modifier is necessary to retain active(s) in the affected locations as to deliver benefits such as dandruff efficacy and itch relief.

Additionally, such an example as above with no or low rheological modifier would not be able to stably suspend many of the type of anti-dandruff agents that are particulate, crystalline actives, including not exclusively sulfur, selenium disulfide and heavy metal salts of pyridinethione such as ZPT. Thus it has been demonstrated that there is a minimum viscosity at lowstress that is necessary to achieve to homogeneity across reasonable time and temperature conditions such that the first through the last applications are delivering the same active concentration.

Also by way of example, it may then be believed that excellent anti-dandruff stability and retention to application site could be achieved by utilizing a high level of rheological modifiers such that the viscosity at low stress is overly sufficient to stabilize dense particulate actives and prevent dripping, running at application. However, the use of a very high level of rheological modifiers to stably suspend actives such as ZPT can negatively affect the ability of the consumer to effectively and easily manipulate the composition from the application sites to cover the affected area such as the scalp.

It has now been discovered that, surprisingly, a balanced approach to among the composition's viscosity at various stresses must be taken, in addition to the necessary composition of carrier and anti-dandruff active. Both are necessary to maximize the effective and stable delivery of anti-dandruff actives from a leave on treatment to an affected area with normal application. It is an object of the present invention to provide treatment compositions, which provide the above balanced combination of anti-dandruff efficacy, coverage, and active stability. These, and other objects, will become readily apparent from the detailed description below.

SUMMARY OF THE INVENTION

In an embodiment of the present invention, it is directed to a scalp care composition comprising from 1% to 99% of a volatile carrier; from 0.05% to 10% of a polymeric rheology modifier and mixtures thereof; from 0.03% to 1% of particulate scalp benefit agent wherein the composition is shear thinning and has (1) a zero shear viscosity value measured at 0.01 Pa of greater than about 1,500 Pa s; (2) a moderate stress viscosity value measured at 1 Pa viscosity of greater than about 1,000 Pa s; and (3) a high shear rate viscosity value measured at 100 l/s of less than about 0.5 Pa s.

These and other features, aspects, and advantages of the present invention will become evident to those skilled in the art from a reading of the present disclosure.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise—both possibilities are suitable for the present invention. Except if stated otherwise, the term "polymer" used herein includes any type of polymer including homopolymers and copolymers.

There is a need for effective treatments of dandruff. Leave-on scalp treatments have the potential to offer certain advantages over rinse-off products such as shampoos: more efficient delivery of the anti-dandruff active to the scalp surface. The most common anti-dandruff actives are particulate materials with relatively high density. This property places certain requirements on the development of effective anti-dandruff leave-on treatments. These treatments should have sufficient viscosity to result in a stable suspension of particles while not being so thick that the product in inhibited from easily flowing throughout the macroscopic and microscopic areas of the scalp surface. A further product benefit is to achieve the product flow that results in this efficient surface coverage without having the product drip off of the scalp surface.

The present invention demonstrates the rheological balance that has been discovered for an anti-dandruff treatment to effectively deliver particulate anti-dandruff actives to the scalp via direct application. Such compositions may have a rheological profile such that the particulate can be stably suspended in the product, then be able to effectively be retained and cover the affected area upon application. In contrast, compositions with low viscosity at low stress can effectively cover the affected area but will not suspend the particulate active, or be retained on the area to which it is applied, leading to poor, uneven/non-homogeneous delivery of the benefit agents. Compositions with high viscosity can suspend the particulate actives and will be retained at the application site, but will be difficult to spread and reach full coverage of the affected area, again leading to poor, uneven/non-homogeneous delivery of the benefit agents. The present invention demonstrates the rheological profile for an anti-dandruff scalp treatment that can be achieved with anti-dandruff active stably suspended in a semi-aqueous carrier system and a polymeric rheological modifier. Such a composition should be shear thinning and have (1) a low stress viscosity measured at 0.01 Pa of greater than 1,500 Pa s, (2) a moderate stress viscosity measured at 1 Pa of greater than 1,000 Pa s and (3) a high shear rate viscosity measured at 100 1/s of less than 0.5 Pa s.

I. Scalp Care Compositions

Solvents

According to an embodiment of the invention, the scalp care composition may include one or more solvents. In an embodiment, the scalp care composition may include one or more organic solvents. Non-limiting examples may include dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

Indole Compounds

The scalp care compositions can further include an indole compound. As used herein, "indole compound" means one or more indoles, derivatives thereof, mixtures thereof, or salts thereof. Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

Xanthine Compounds

The scalp care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In an embodiment, the amount of xanthine may be decreased to lessen potential white residue the may result from various formulations when the xanthine is present in higher amounts. In an embodiment, the hair care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. In an embodiment, the hair care composition may have no xanthine.

Vitamin $B_3$ Compounds

The scalp care compositions can further include a vitamin B3 compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. In one embodiment, the composition may include from about 0.1% to about 25% of the vitamin $B_3$ compound; in a further embodiment, from about 0.1% to about 15% of the vitamin $B_3$ compound; in a further embodiment, from about 0.1% to about 7.5%, in another embodiment, from about 3.5% to about 7.5% of the vitamin $B_3$ compound, for example, wherein the percentage is a weight percentage based on the total weight of the final hair care composition. In an embodiment, the scalp care composition may further include about 2.5% of vitamin $B_3$.

Panthenol Compounds

The scalp care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, in one embodiment, the composition may include from about 0.01% to about 5% of the panthenol compound, in another embodiment, the composition may include from about 0.01% to 2.% of the panthenol compound, in a further embodiment, the composition may include from about 0.05% to about 2% of the panthenol compound; and in another embodiment, the composition may include from about 0.1% to about 1% of the panthenol compound, for example, wherein the percentage is a weight percentage based on the total weight of the final hair care composition. In a further embodiment, the scalp care composition may further include about 0.15% of panthenol.

According to another aspect of the present invention, the scalp care compositions may be free of oleanolic acid and/or biotinyl-GHK, which is contrary to that described in U.S. Patent Application No. 20060067905.

Rheology Modifier

In one embodiment, the scalp care composition comprises a rheology modifier to increase the substantivity of the composition. Any suitable rheology modifier can be used. In an embodiment, the scalp care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the scalp care composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogens copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a further embodiment, the rheology modifiers may be alginic acid based materials, non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polypolyacrylates, hydrophobically modified polyacrylic acids, and hydrophobically modified polyacrylamides; Hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives, nonlimiting examples include Microcrystalline cellulose; Carboxymethylcelluloses; Hydroxyethylcellulose; Hydroxypropylcellulose; Hydroxypropylmethylcellulose; Methylcellulose; ethyl cellulose; nitro cellulose; cellulose sulfate; cellulose powder; Hydrophobically modified celluloses In an embodiment, the rheology modifier may be a guar and guar derivatives, non-limiting examples include hydroxypropyl guar, and hydroxypropyl guar hydroxypropyl trimonium chloride.

In an embodiment, the rheology modifier may be polyethylene oxide; polypropyne oxide; and POE-PPO copolymers.

In an embodiment, the rheology modifier may be polyvinylpyrrolidone, crosslinked polyvinylpyrrolidone and derivatives. In a further embodiment, the rheology modifier may be Polyvinyalcohol and derivatives.

In a further embodiment, the rheology modifier may be polyethyleneimine and derivatives.

In another embodiment, the rheology modifier may be silicas, non-limiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums non-limiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquarternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol Ultrez 30, Carbopol 1342, Sepigel™ 305, Simulgel™600, Sepimax Zen, and combinations thereof.

Carrier

According to another aspect of the present invention, the scalp care compositions may further include at least about 20 weight percent of an aqueous carrier. According to one embodiment, the aqueous carrier may be prepared from demineralized or distilled water, for example. In an embodiment of the present invention, the carrier may comprise water, organic solvents (miscible or non-miscible with water), silicone solvents or a mixture thereof. In one embodiment of the present invention, a volatile carrier may include water or a mixture of water and organic solvents. In a further embodiment, the solvents may be dermatologically acceptable. In a further embodiment, the carrier may comprise water with minimal or no significant concentrations of organic solvent, except as otherwise incidentally incorporated into the composition as minor ingredients of other components. In another embodiment, water, organic and silicone solvents that have boiling points below or equal to 250° C. may be volatile solvents and volatile carriers. In one embodiment, solvents with boiling points above 250° C. may be considered non-volatile.

Non-limiting examples of a carrier may include water and water solutions of lower alkyl alcohols and polyhydric alcohol, the lower alkyl alcohols such as monohydric alcohols having 1 to 6 carbons, in one aspect, ethanol and isopropanol, and polyhydric alcohols such as glycols, glycerine and other diols.

Other acceptable carriers that may be used in the aqueous carrier include, but are not limited to alcohol compounds, such as ethanol. According to one embodiment, the composition comprises alcohol, dipropylene glycol, and/or water.

The scalp care compositions may have a pH ranging from about 3.0 to about 10, which may be measured by taking a direct pH measurement using a standard hydrogen electrode of the composition at 25° C. Accordingly, the pH of the hair care composition may be within the range from about 4 to about 9, as a non-limiting example.

Scalp Benefit Agent

In an embodiment of the present invention, the composition may comprise a scalp benefit agent, a non-limiting example being an anti-dandruff active, which may be an anti-dandruff active particulate. In an embodiment, the anti-dandruff active is selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5%, in a further embodiment 0.2% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2x\ A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Polyols

Polyols are a component of the present invention. In an embodiment of the present invention, a nonlimiting example of a polyol is glycerin. Glycerin is a colorless, odorless, viscous liquid that is very common for use in personal care applications and pharmaceutical formulations. Glycerin contains three hydroxyl groups that are responsible for its solubility in water and its humectant nature. Glycerin is well known as hair and skin benefit agent in personal care applications. This material can penetrate into a human hair to provide conditioning and softness via plasticization of the hair fiber while maintaining a very clean surface feel. Glycerin has been observed to clean more hydrophobic soil components (ie. sebum) than water.

The levels of Glycerin range from about 0.1% to about 10%, from about 0.5% to about 8%, from about 1% to about 7% and from about 3.0% to about 6.0% by weight of the shampoo composition.

In another embodiment of the present invention, other polyols may be used. Nonlimiting examples include propylene glycol, sugar polyols such as sorbitol, aloe vera gel and honey.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the shampoo compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Scalp Health Actives

In an embodiment of the present invention, a scalp health active may be added to provide scalp benefits in addition to the the anti-fungal/anti-dandruff efficacy provided by the ZPT. This group of materials is varied and provides a wide range of benefits including moisturization, barrier improvement, anti-fungal, and anti-oxidant, anti-itch, and sensates. Such skin health actives include but are not limited to: vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, iso cyclomone, benzyl alcohol, and natural extracts/oils including peppermint, spearmint, argan, jojoba and aloe.

Optional Ingredients

The compositions of the present invention can also additionally comprise any suitable optional ingredients as desired. For example, the composition can optionally include other active or inactive ingredients.

The compositions may include other common hair ingredients such as pyrithione zinc, minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, *eucalyptus* oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

II. Methods

Analytical ZPT Stability and Viscosity Study

The present invention has determined the viscosity range necessary to suspend ZPT particles and maintain stability over time at multiple temperature conditions. Further, the present invention can demonstrate ZPT stability within the present scalp care compositions.

A composition is formulated to different viscosities ranging from less than 100 cps to 10,000 cps using increasing levels of pH neutralizer. The formulations are then placed at constant temperature for in the range of prototypes in the 5 C, 25 C, and 40 C CT (controlled temperature) rooms for 1 month period of time in a package container representative of one that could readily dispense a scalp care product and then samples of each bottle are obtained at the top, middle, and bottom and tested for ZPT content. Additionally, each sample is graded on a visual sedimentation scale.

Viscosity—Throughout the data discussion below, "viscosity" is used to indicate the viscosity in centipoises (cps) measured on a Brookfield Rheometer RS with Cone C75-1 at 26.7 C using a 2.5 mL sample a constant shear rate of 2 l/s for 3 minutes. This method was performed after the sample was removed from its respective controlled temperature room and allowed to return to ambient conditions for a time no less than 3 hours. "Initial viscosity" is measured on day 0, before prototypes were placed in CT rooms to age.

Visual Sedimentation Scale—Prototypes are filled into 2 oz glass jars and kept at approximately 25 C for 2 weeks, then visually graded on the homogeneity across the height of the bottle. The grading scale used is from 0-3 where 0=visually homogeneous from top to bottom, no sedimentation and 3=significant differences between the top and the bottom, significant sedimentation.

Product Sampling Protocol—Remove samples from their respective CT rooms. Pierce the side of the packaging at the indicated points with a needle and insert to approximately the center of the bottle, ~20 mm. Beginning with the "bottom" sample at ~5 mm from the bottom of the bottle, remove ~20 ml of product and place in a glass vial. Repeat with the "middle" sample at 45 mm and "top" sample at 85 mm.

ZPT detection method—This method is used to analyze the % zinc pyrithione (ZPT) in Leave on Treatments. The pyrithione is titrated with iodine by an autotitrator with the endpoint of the titration determined using a combination platinum ring electrode.

Results

| | Product Example | | | | | |
|---|---|---|---|---|---|---|
| | 1A | | | 1B | | |
| | Initial Viscosity (cps) | | | | | |
| | <100 cps | | | 518 | | |
| | Visual Grading | | | | | |
| | | 3 | | | 2 | |
| Location | Top | Middle | Bottom | Top | Middle | Bottom |
| 1 Month Viscosity (cps) | <100 | <100 | <100 | 555 | 524 | 684 |
| ZPT Content (%) @5° C. | 0.01 | 0 | 0.06 | 0.05 | 0.07 | 0.1 |
| ZPT Content (%) @25° C. | 0.02 | 0.02 | 0.06 | 0.07 | 0.07 | 0.1 |
| ZPT Content (%) @40° C. | 0.02 | 0.02 | 0.09 | 0.07 | 0.07 | 0.09 |
| Average | 0.017 | 0.013 | 0.070 | 0.063 | 0.070 | 0.097 |
| | | Not Stable | | | Not Stable | |

-continued

| | Product Example | | | | | |
|---|---|---|---|---|---|---|
| | 1C | | | 1D | | |
| | Initial Viscosity (cps) | | | | | |
| | 1104 | | | 1749 | | |
| | Visual Grading | | | | | |
| Location | Top | 0 Middle | Bottom | Top | 0 Middle | Bottom |
| 1 Month Viscosity (cps) | 1171 | 910 | 1372 | 1946 | 1820 | 1775 |
| ZPT Content (%) @5° C. | 0.09 | 0.09 | 0.09 | 0.09 | 0.09 | 0.09 |
| ZPT Content (%) @25° C. | 0.09 | 0.09 | 0.09 | 0.09 | 0.09 | 0.09 |
| ZPT Content (%) @40° C. | 0.09 | 0.09 | | 0.09 | 0.09 | 0.09 |
| Average | 0.090 | 0.090 Stable | 0.090 | 0.090 | 0.090 Stable | 0.090 |

Product 1A is Example 1 of the example table below with the exception that the Neutrol Te is at 0.00%. Product 1B is the same composition as Example 1 of the example table below with the exception that the Neutrol TE is at 0.06%. Product 1c is the same composition as Example 1 of the example table below with the exception that the Neutrol TE is at 0.075%. Product 1B is the same composition as Example 1 of the example table below with the exception that the Neutrol TE is at 0.09%.

To maintain ZPT suspension over 1 month at 5 C, 25 C, and 40 C, a viscosity as measured at a shear of 2 1/sec of 1000 cps or higher is required. At lower viscosities, the dense ZPT particles will settle to the bottom of the packaging, leading to differences in anti-dandruff active concentration across the package Consumer Research Panel Assessment of Scalp Care Leave on Treatment Usage The objective of this study is to determine the panelist perception or dripping, coverage, and spread for three scalp treatments that encompass a low, balanced, and high rheological profile.

Methodology:

Panelist Recruitment—The panelist group is made up of 20 individuals, 50:50 male:female, ranging in age from 18-55. Panelists are familiar with use of scalp leave on treatments though not specifically those included in the study.

Products—All products were assessed by each panelist in a random order and were blinded using the codes below.

1. Product 1 (low viscosity example)→Scalp treatment Liquid
2. Product 2 (high viscosity example)→Scalp styling cream
3. Product 3 (balanced example)→Present Invention scalp treatment (See Example 1)

Product 1 is a commercially available comparative product containing the following ingredients: salicylic acid, water, alcohol denatured, propylene glycol, menthol, aloe barbadensis leaf extract, melaleuca alternifolia leaf oil, tocopheryl acetate.

Product 2 is a commercially available comparative product containing the following ingredients: pyrithione zinc, water, cetostearyl alcohol, steareth-20, propylene glycol, PPG-5-ceteth-20, isopropyl palimitate, copovidone K-25-31, steareth-2, glycerin, DMDM hydantoin, PEG-100 stearate, butylens glycol, trideceth-6, iodopropynyl butylcarbamate, FD&C Blue No. 1.

Each panelist completed three different stations, completing the questionnaire for all three products after each station.

Station 1—A quantity of 0.5-1.0 mL of each product is applied ad lib to the top of 6 inch skin mimic section that is held at a 30 degree angle. The skin mimic could be a polyurethane substrate with texture, surface energy and charge of human inner-forearm. It is made by casting liquid urethane in a metal mold to generate forearm texture, then applying plasma surface modification to create specific surface energy and charge of forearm skin. After applying all of the products to the skin mimic, panelists observe from approximately 5 sec, then complete the questionnaire. Skin mimics are cleaned with 70:30 ethanol between panelist usages.

Question 1: The amount that the product drips (1=no dripping, 5=extreme dripping)

Question 2: The ability of the product to stay where it is put (1=stays in place very much, 5=stays in place not at all)

Station 2—A quantity of 0.5-1.0 mL of the product is applied ad lib to a one third section of a 6 in×3 in skin mimic. Panelist apply the first product then take two fingers and rub the product in to cover the designated area. Panelist clean off their fingers and repeat with the second and third products. After assessing all products, they complete the questionnaire. Skin mimics are cleaned with 70:30 ethanol between panelist usages.

Question 3: The ease of spread the product (1=easy to spread, 5=difficult to spread)

Question 4: The ability of the product to cover the area (1=easy to cover, 5=difficult to cover)

Station 3—A quantity of 2.0-5.0 mL of the product is applied ad lib to the crown of a manikin head with damp hair that is between 10-24 inches long. Product is applied in three lines, one down the middle and one down each of the left and right sides, and panelists use both hands to rub the product into the hair and scalp. They clean off their fingers and repeat with the second and third products on separate manikin heads. After assessing all products, they complete the questionnaire. Manikin heads and hair are cleaned with non-conditioning shampoo between panelist usages.

Question 1: The ease of dispensing the product (1=dispenses easily, 5=difficult to dispense)

Question 2: The amount that the product drips (1=no dripping, 5=extreme dripping)

Questions 3: The ability of the product to stay where it is put (1=stays in place very much, 5=stays in place not at all)

Question 4: The ease of spread the product (1=easy to spread, 5=difficult to spread)

Question 5: The ability of the product to cover the scalp (1=easy to cover, 5=difficult to cover)

Statistical Analysis—Analysis of means is completed using JMP software and means are compared via Student's t LSD at 95% confidence.

Results:

Dripping and Retention to Application Site—On both the skin mimic and manikin head, panelist observe the low viscosity product (1) to be significantly more dripping and significantly less ability to stay where it is applied. Thus when applied to the affected area, the low viscosity Product 1 is significantly more likely to drip, run, or transfer to another surface, thus removing the active ingredient from where it is applied and making the product less effective.

|  | Dripping (on skin mimic) | | Retention (on skin mimic) | | | Dripping (on manikin head) | | Retention (on manikin head) | |
|---|---|---|---|---|---|---|---|---|---|
| Product 1 | A | 4.90 | A | 4.93 | Product 1 | A | 4.63 | A | 4.40 |
| Product 3 | B | 1.83 | B | 1.78 | Product 3 | B | 1.73 | B | 1.93 |
| Product 2 | C | 1.08 | C | 1.03 | Product 2 | C | 1.08 | C | 1.13 |

* Levels not connected by the same letter are significantly different (a = 0.05)

Ability to Spread and Cover Application Site—On both the skin mimic and manikin head, panelist observe the high viscosity Product 2 to be significantly more difficult to spread, and cover the application site. Thus when applying, the high viscosity Product 2 is significantly more difficult to spread out and cover the affected area, thus leading to uneven and inhomogeneous coverage with the scalp benefit agent.

|  | Spread (on skin mimic) | | Area Coverage (on skin mimic) | | | Spread (on manikin head) | | Scalp Coverage (on manikin head) | |
|---|---|---|---|---|---|---|---|---|---|
| Product 2 | A | 2.73 | A | 2.65 | Product 2 | A | 3.55 | A | 3.93 |
| Product 3 | B | 1.53 | B | 1.50 | Product 1 | B | 2.43 | B | 2.65 |
| Product 1 | B | 1.48 | B | 1.35 | Product 3 | B | 2.00 | B | 1.93 |

* Levels not connected by the same letter are significantly different (a = 0.05)

Two specific points of contact within the consumer usage experience will dictate the effective delivery of scalp benefit agents from a scalp treatment. The first is the retention of the product at the site of application. If the product runs, drips, or transfers to other surfaces easily (as with Product 1), it will carry the scalp benefit agents away from where it is needed most, leading to uneven and inhomogeneous delivery and thus reduced efficacy. The second is the ability of the product to cover the affected area completely. If it is difficult to spread the product on the skin and through the hair (as with Product 2), the scalp treatment agent will not come into contact with all of the affected area, again leading to uneven and inhomogeneous delivery and thus reduced efficacy. Thus it has been determined that there is middle range of viscosity/rheology that is needed to balance retention and coverage as with Product 3 representative of the present invention.

Product 1 it is believed has no rheology modifier and it is believed that is why it does not provide the benefit that the present invention does. Product 2 it is believed could not be working due to not having the proper amount of a rheology modifier and does not provide the benefit that the present invention provides.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Examples

|  | Examples | | | | | | | Comparative Examples | |
|---|---|---|---|---|---|---|---|---|---|
|  | 1 Active wt %) | 2 Active wt % | 3 Active wt % | 4 Active wt % | 5 Active wt % | 6 Active wt % | 7 Active wt % | 8 Active wt % | 9 Active wt % |
| Water | Q.S. | QS | QS | QS | QS | QS | QS | Q.S. | Q.S. |
| Alcohol 100% (Ethanol) | 50 | 50 | 0 | 50 | 60 | 25 | 0 | 50 | 50 |
| Isopropyl Alcohol | 0 | 0 | 0 | 0 | 0 | 0 | 0 | 0 | 15 |
| Acrylates/C10-30 alkyl acrylate crosspolymer *1 | 0.35 | 0.5 | 0.2 | 0 | 0 | 0 | 0 | 0.03 | 0 |
| Carbomer *2 | 0 | 0 | 0 | 0 | 0 | 0 | 0 | 0 | 0 |
| Polyacrylamide *3 | 0 | 0 | 0 | 0.5 | 0 | 0 | 0 | 0 | 0 |
| C13-14 Isoparaffin *3 | 0 | 0 | 0 | 0.5 | 0 | 0 | 0 | 0 | 0 |
| Laureth 7 *3 | 0 | 0 | 0 | 0.1 | 0 | 0 | 0 | 0 | 0 |
| Polyacrylate crosspolymer-6 *4 | 0 | 0 | 0 | 0 | 0.5 | 0 | 0 | 0 | 0 |
| Dehydroxanthan Gum *5 | 0 | 0 | 0 | 0.25 | 0 | 0 | 0 | 0 | 0 |
| Cetyl Alcohol, Sodium Polyacrylate, Glyceryl Stearate, Polysorbate 80, and Caprylic/Capric Triglycerinde *6 | 0 | 0 | 0 | 0 | 0 | 2.5 | 0 | 0 | 0 |
| Acrylates/Aminoacrylates/ C10-30 Alkyl PEG-20 Itaconate Copolymer *7 | 0 | 0 | 0 | 0 | 0 | 0 | 1.5 | 0 | 0 |

-continued

|  | Examples | | | | | | | | Comparative Examples | |
|---|---|---|---|---|---|---|---|---|---|---|
|  | 1 Active wt %) | 2 Active wt % | 3 Active wt % | 4 Active wt % | 5 Active wt % | 6 Active wt % | 7 Active wt % | — | 8 Active wt % | 9 Active wt % |
| Zinc pyrithione *8a | 0.1 | 0.2 | 0.07 | 0.1 | 0.1 | 0.1 | 0.1 |  | 0.1 | 0.1 |
| Zinc carbonate *8b | 0 | 0.2 | 0 | 0 | 0 | 0 | 0 |  | 0 | 0 |
| PEG/PPG 20/23 Dimethicone 430 *9 | 0 | 1 | 0 | 0 | 0 | 0 | 0 |  | 0 | 0 |
| Bis-PEG/PPG-16/16 PEG/PPG 16/16 Dimethicone *10 | 0.7 | 0 | 0 | 1 | 0 | 0 | 0 |  | 1 | 0 |
| Polyquaternium-4 *111 | 0 | 0 | 0 | 0 | 0 | 0 | 1 |  | 0 | 0 |
| Panthenol | 0.15 | 0.5 | 0 | 0.15 | 0 | 0 | 0 |  | 0.1 | 0 |
| Niacinamide | 2.5 | 0 | 0 | 3 | 0 | 0 | 0 |  | 2 | 0 |
| Caffeine | 0.75 | 0 | 0 | 1.25 | 0 | 0 | 0 |  | 0.5 | 0 |
| Glycerin | 0.5 | 5 | 0 | 5 | 0 | 0 | 0 |  | 0 | 0 |
| Argania Spinosa Kernel Oil *12 | 0 | 0 | 0 | 0 | 0 | 0 | 0 |  | 0 | 0 |
| Propylene Glycol | 0 | 0 | 1 | 0 | 0 | 0 | 0 |  | 0 | 1 |
| Menthol | 0 | 0 | 0.5 | 0 | 0 | 0 | 0 |  | 0 | 0.3 |
| Polyvinylpyrrolidone *13 | 0 | 1 | 0 | 0 | 0 | 0 | 0 |  | 0 | 0 |
| Polyethylene Low Density Powder *14 | 0 | 0.5 | 0 | 0 | 0 | 0 | 0 |  | 0 | 0 |
| Tapicoa Starch Polymethylsilsesuioxane *15 | 0 | 0 | 1 | 0 | 0 | 0 | 0 |  | 0 | 0 |
| Benzyl Alcohol | 0 | 0 | 0.5 | 0 | 0 | 0 | 0 |  | 0 | 0 |
| Methylisothiazolinone *16 | 0 | 0 | 0.05 | 0 | 0 | 0 | 0 |  | 0 | 0 |
| PEG-40 Hydrogenated Castor Oil *17 | 0 | 0 | 0.5 | 0 | 0 | 0 | 0 |  | 0 | 0 |
| Tetrahydroxypropyl Ethylenediamine *18 | 0.12 | 0 | 0.14 | 0 | 0 | 0 | 0 |  | 0.05 | 0.05 |
| Triethanolamine *19 | 0 | 0.1 | 0 | 0 | 0 | 0 | 0 |  | 0 | 0 |
| Glycolic Acid *20 | 0 | 0 | 0 | 0 | 0 | 0 | 0.25 |  | 0 | 0 |
| Citric Acid | 0 | 0 | 0 | 0.008 | 0.005 | 0.005 | 0.005 |  | 0 | 0 |

*1 as in Carbopol Ultrez 21 available from Lubrizol
*2 as in Carbopol Ultrez 30 available from Lubrizol
*3 as in Sepigel 305 from Seppic
*4 as in SepiMax Zen from Seppic
*5 as in Amaze XT from AkzoNovel
*6 as in Jeesperse CPW-CG-02 from Jeen
*7 as in Structure Plus from Akzo Nobel
*8a as in ZPT from Lonza Personal Care
*8b as in Zinc carbonate from Brueggemann Chemical
*9 as in Silsoft 430 Dimethicone Copolyol from Momentive
*10 as in Abil Care 85 from Evonik
*11 as in Celquat H-100 from Akzo Nobel
*12 as in Lipofructyl Argan LS9779 from BASF
*13 as in PVP K-30 from ISP Technologies
*14 as in Microthene FN 510-00 from Equistar Chemicals
*15 as in Dry Flo TS from Akzo Nobel
*16 as in Neolone 950 from Rohm and Haas
*17 as in Cremophor RH-40 Surfactant from BASF
*18 as in Neutrol Te from BASF
*19 as in Trolamine from Dow Chemical
*20 as in Glypure from DuPont Examples 1-7 are representative of the present invention. Example 8 and Example 9 are comparative examples. Example 8 would not deliver the desired benefit that the present invention delivers because it is believed that it would not contain sufficient amount of a rheology modifier. Example 9 would not deliver the desired benefit that the present invention delivers because it is believed to be missing the desired rheological modifier.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

Viscosity Test Method

Method which Provides a Zero Shear Viscosity Value

A zero shear viscosity as related to sedimentation and stability can be measured using the following method:

The viscosity of the scalp care composition may be determined by a cone and plate viscometer/rheometer which measures the viscous drag resulting from the sample material contained in the gap between a rotating cone and a stationary plate. The geometry of the cone and plate may be such that the entire sample is subjected to a uniform shear rate. To determine the relevant viscosity for stability and sedimentation an Advanced Rheometer 2000 fitted with a 4 degree, 6 centimeter Acrylic cone at 25 C temperature using a 3.95 mL sample size and a solvent trap may be used with a procedure consists of a 2 minute relaxation time, followed by a constant stress creep step at 0.01 Pa. Using Stokes law, it can be calculated that the stress from gravity (sedimentation) on a particle with a radius of 2 micrometers and density 1800 kg/m$^3$ in a fluid of density 920 kg/m$^3$ can be approximated as 0.01 Pa. Shear rate is then determined by fitting a straight line through the strain versus time data collected from 60 seconds through 240 seconds using the Rheology Advantage Data Analysis package and viscosity at the specified stress is then calculated by stress/rate in Pa s. In an embodiment of the present invention, the composition has a zero shear viscosity measured at 0.01 Pa of greater than about 1,500 Pa s, in a further embodiment, a zero shear viscosity measured at 0.01 Pa of greater than about 2,000 Pa s, in yet a further embodiment, a zero shear viscosity measured at 0.01 Pa of greater than about 10,000 Pa s.

Method which Provides a Moderate Stress Viscosity Value

A moderate stress viscosity as related to dripping of a scalp care composition can be measured using the following method:

The viscosity of the scalp care composition may be determined by a cone and plate viscometer/rheometer which measures the viscous drag resulting from the sample material contained in the gap between a rotating cone and a stationary plate. The geometry of the cone and plate may be such that the entire sample is subjected to a uniform shear rate. To determine the relevant viscosity for dripping, an Advanced Rheometer 2000 fitted with a 4 degree, 6 centimeter Acrylic cone at 25 C temperature using a 3.95 mL sample size and a solvent trap may be used with a procedure consists of a 2 minute relaxation time, followed by application of a constant stress of 1 Pa. A stress of approximately 1 Pa can be calculate based upon the stress from gravity of a droplet of fluid of density 920 kg/m$^3$ on an angle such as one of 45 degrees. Shear rate is then determined by fitting a straight line through the strain versus time data collected from 60 seconds through 240 seconds using the Rheology Advantage Data Analysis package and viscosity at the specified stress is then calculated by stress/rate in Pa s. In an embodiment of the present invention, the composition has a moderate stress viscosity measured at 1 Pa of greater than about 1,000 Pa s, in a further embodiment, a moderate stress viscosity measured at 1 Pa of greater than about 1,500 Pa s, and yet in a further embodiment, a moderate stress viscosity measured at 1 Pa of greater than about 5000 Pa s.

Method which Provides a High Shear Rate Viscosity Value

A high shear rate viscosity as related to spreading of a scalp care composition can be measured using the following method:

The viscosity of the hair care composition may be determined by a concentric cylinder or cup and bob viscometer/rheometer which measures the viscous drag resulting from the sample material contained in the gap between a rotating bob and a stationary cup. To determine the relevant viscosity for spreading, an Advanced Rheometer 2000 can be fitted with an aluminum bob of diameter 28 mm and cup of diameter 30 mm is held at 25 C temperature and a sample volume of 19.6 mL. The procedure consists of a 2 minute relaxation time, followed by a peak flow hold at a constant shear rate of 100 l/s to approximate the rate at which product may be massaged into the affected area. Viscosity is measured every 10 seconds over a 1 minute time period and the Rheology Advantage Data Analysis package is used to calculate the mean viscosity in Pa s. In an embodiment of the present invention, the composition has a high shear rate viscosity measured at 100 l/s of less than about 0.5 Pa s, in a further embodiment, a high shear rate viscosity measured at 100 l/s of less than about 0.3 Pa s, and in yet a further embodiment, a high shear rate viscosity measured at 100 l/s of less than about 0.1 Pa s.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A leave-on scalp care composition comprising:
  a) from about 1% to about 99% of a volatile carrier wherein the volatile carrier comprises an organic solvent selected from the group consisting of dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, 1,6-hexanediol and combinations thereof;
  b) from about 0.05% to about 10% of one or more polymeric rheology modifiers;
  c) from about 0.03% to about 1% of particulate scalp benefit agent wherein the composition is shear thinning and has (1) a zero shear viscosity value measured at 0.01 Pa of greater than about 1,500 Pa s; (2) a moderate stress viscosity value measured at 1 Pa of greater than about 1,000 Pa s; and (3) a high shear rate viscosity value measured at 100 l/s of less than about 0.5 Pa s.

2. A scalp care composition according to claim 1 wherein the polymeric rheology modifier is selected from the group consisting of homopolymers of acrylic acid, methacrylic acid and derivatives, alkali swellable and hydrophobically-modified alkali swellable acrylic copolymers or methacrylate copolymers, crosslinked acrylic polymers, and associative polymeric thickeners and mixtures thereof.

3. A scalp care composition according to claim 2 wherein the polymeric rheology modifier is an acrylates/C10-C30 alkyl acrylate crosspolymer.

4. A scalp care composition according to claim 2 wherein the polymeric rheology modifier is a crosslinked acrylic polymer.

5. A scalp care composition according to claim 1 wherein the particulate scalp benefit agent is selected from the group consisting of metal pyridinethione salts, selenium sulfide, particulate sulfur, and mixtures thereof.

6. A scalp care composition according to claim 1 wherein particulate scalp benefit agent is zinc pyrithione.

7. A scalp care composition according to claim 1 wherein the composition further comprises glycerin.

8. A scalp care composition according to claim 1 wherein the composition further comprises niacinamide in the range of 0.1% to 7.5%.

9. A scalp care composition according to claim 1 wherein the composition further comprises caffeine in the range of 0.1% to 3.0%.

10. A scalp care composition according to claim 1 wherein the composition further comprises panthenol in the range of 0.01% to 2.0%.

11. A scalp care composition according to claim 1 wherein the composition further comprises a silicone.

12. The leave-on scalp care composition according to claim 1 wherein the composition is a leave-on composition wherein the leave-on composition is applied to keratinous tissue and allowed to remain on the keratinous tissue.

* * * * *